(12) United States Patent
Kruse et al.

(10) Patent No.: US 9,693,973 B2
(45) Date of Patent: *Jul. 4, 2017

(54) ACTIVE SUBSTANCE COMBINATION OF LICOCHALCONE A AND PHENOXYETHANOL

(71) Applicants: Inge Kruse, Hamburg (DE); Thomas Raschke, Pinneberg (DE); Jens-Peter Vietzke, Hamburg (DE); Julia Eckert, Hamburg (DE)

(72) Inventors: Inge Kruse, Hamburg (DE); Thomas Raschke, Pinneberg (DE); Jens-Peter Vietzke, Hamburg (DE); Julia Eckert, Hamburg (DE)

(73) Assignee: BEIERSDORF AG, Hamburg (DE)

(*) Notice: Subject to any disclaimer, the term of this patent is extended or adjusted under 35 U.S.C. 154(b) by 22 days.

This patent is subject to a terminal disclaimer.

(21) Appl. No.: 14/604,949

(22) Filed: Jan. 26, 2015

(65) Prior Publication Data

US 2015/0141522 A1 May 21, 2015

Related U.S. Application Data

(60) Continuation of application No. 11/514,214, filed on Sep. 1, 2006, now Pat. No. 8,969,418, which is a division of application No. 11/001,224, filed on Dec. 2, 2004, now abandoned.

(30) Foreign Application Priority Data

Dec. 2, 2003 (DE) .................... 103 56 164

(51) Int. Cl.
| | |
|---|---|
| *A61K 31/075* | (2006.01) |
| *A61K 31/12* | (2006.01) |
| *A61K 36/484* | (2006.01) |
| *A61K 31/47* | (2006.01) |
| *A61K 31/085* | (2006.01) |
| *A61K 8/35* | (2006.01) |
| *A61K 8/97* | (2017.01) |
| *A61Q 19/00* | (2006.01) |
| *A61Q 19/08* | (2006.01) |
| *A61K 8/34* | (2006.01) |
| *A61K 31/047* | (2006.01) |

(52) U.S. Cl.
CPC ............. *A61K 31/12* (2013.01); *A61K 8/34* (2013.01); *A61K 8/345* (2013.01); *A61K 8/35* (2013.01); *A61K 8/97* (2013.01); *A61K 31/047* (2013.01); *A61K 31/075* (2013.01); *A61K 31/085* (2013.01); *A61K 36/484* (2013.01); *A61Q 19/00* (2013.01); *A61Q 19/005* (2013.01); *A61Q 19/007* (2013.01); *A61Q 19/08* (2013.01)

(58) Field of Classification Search
CPC .. A61K 2300/00; A61K 31/075; A61K 31/12; A61K 36/484; A61K 31/47; A61K 31/85; A61K 8/34; A61K 8/345; A61K 8/35; A61K 8/97; A61Q 19/00; A61Q 19/005; A61Q 19/007; A61Q 19/08

See application file for complete search history.

(56) References Cited

U.S. PATENT DOCUMENTS

| | | | |
|---|---|---|---|
| 4,144,325 | A | 3/1979 | Voyt |
| 4,954,532 | A | 9/1990 | Elliot et al. |
| 5,422,112 | A | 6/1995 | Williams |
| 5,690,948 | A | 11/1997 | McCook et al. |
| 6,214,352 | B1 | 4/2001 | Matsukawa |
| 8,470,349 | B2 | 6/2013 | Tom Dieck et al. |
| 9,017,707 | B2 | 4/2015 | Tom Dieck et al. |
| 2002/0001599 | A1 | 1/2002 | Neubourg |
| 2004/0044077 | A1 | 3/2004 | Katagiri et al. |
| 2005/0037042 | A1 | 2/2005 | Tom Dieck et al. |
| 2007/0196289 | A1 | 8/2007 | Blatt et al. |
| 2013/0253068 | A1 | 9/2013 | Tom Dieck et al. |

FOREIGN PATENT DOCUMENTS

| | | |
|---|---|---|
| DE | 0224387 | 12/2003 |
| EP | 0998939 A1 | 5/2000 |
| EP | 1354480 A2 | 10/2003 |
| EP | 1354580 A1 | 10/2003 |
| EP | 1541152 A1 | 6/2005 |
| JP | 1157909 * | 6/1989 |
| JP | 62181202 | 8/1997 |
| JP | 2001163718 A | 6/2001 |
| JP | 2003238379 | 8/2003 |
| WO | 03101414 A1 | 12/2003 |
| WO | 2005027866 A1 | 3/2005 |
| WO | 2005030157 A1 | 4/2005 |

OTHER PUBLICATIONS

Saeedi et a;. "The treatment of atopic dermatitis with licorice gel" Journal of Dermatological Treatment, Sep. 2003, vol. 14, No. 3, pp. 153-157.

Mitchell et al. "Phenoxyethanol is effective topical therapy of Gram-negative cellulitis in neutropenic patients", Journal of Hospital Injection, 1993, vol. 25, pp. 53-56.

P.J. Frosch and A.M. Kligman, J. Soc. Cosmet, Chem., 28, 197-209 (May 1977).

A. Deflandre and G. Lang, International Journal of Cosmetic Science, 10, 53-62 (1988).

A. Voelckel et al., Zentralblatt Haut- und Geschlechtskrankheiten, 156, 1-15 (1989).

Y. Miyachi "Skin Diseases Associated with Oxidative Injury" in "Oxidative Stress in Dermatology", edited by Fuchs and L. Packer, (Continued)

*Primary Examiner* — Kendra D Carter
(74) *Attorney, Agent, or Firm* — Abel Law Group, LLP

(57) ABSTRACT

Disclosed is a method for the treatment or prophylaxis of an inflammatory skin condition with cosmetic or pharmaceutical preparation which comprises licochalcone A and phenoxyethanol.

14 Claims, No Drawings

(56) References Cited

OTHER PUBLICATIONS

Marcel Dekker, Inc., new York, Basel, Hong Kong, 1993, pp. 323-331.

* cited by examiner

ACTIVE SUBSTANCE COMBINATION OF LICOCHALCONE A AND PHENOXYETHANOL

CROSS-REFERENCE TO RELATED APPLICATIONS

The present application is a continuation of U.S. application Ser. No. 11/514,214, filed Sep. 1, 2006, which is a divisional of U.S. application Ser. No. 11/001,224, filed Dec. 2, 2004, which claims priority under 35 U.S.C. §119 of German Patent Application No. 103 56 164.1, filed Dec. 2, 2003. The disclosures of the parent U.S. applications and the German priority application are expressly incorporated by reference herein in their entireties.

BACKGROUND OF THE INVENTION

1. Field of the Invention

The present invention relates to cosmetic or dermatological preparations containing active substances for the care and protection of the skin, in particular sensitive skin, as well as skin aged or aging through intrinsic and/or extrinsic factors and the use of such active substances and combinations of such substances in the field of cosmetic and dermatological skin care.

2. Discussion of Background Information

Cosmetic skin care is primarily understood as meaning that the natural function of the skin as a barrier against environmental influences (e.g. dirt, chemicals, micro-organisms) and against the loss of substances intrinsic to the body (e.g. water, natural fats, electrolytes) is strengthened or restored. Impairment of this function may lead to increased absorption of toxic or allergenic substances or to attack by microorganisms, resulting in toxic or allergic skin reactions.

For example, in the case of aged skin, a regenerative restoration occurs slowly, whereby in particular the capacity of the horny layer of the epidermis to bind water diminishes. For this reason, the skin becomes inflexible, dry, and cracked ("physiologically" dry skin). The consequence is a barrier damage. The skin becomes susceptible to negative environmental influences, such as the invasion of microorganisms, toxins, and allergens, possibly resulting in even toxic or allergic skin reactions.

In the case of pathologically dry and sensitive skin, barrier damage exists a priori. Epidermal intercellular lipids become deficient or develop in an inadequate quantity or composition. The consequence is an increased permeability of the horny layer and an inadequate protection of the skin against loss of hygroscopic substances and water.

The barrier effect of the skin can be quantified by determining the transepidermal water loss (TEWL). This process involves the evaporation of water from the interior of the body without including the loss of water during perspiration. The determination of the TEWL value has proven to be extremely informative, and may be used for diagnosing cracked or chapped skin, for determining the compatibility of chemically differently composed surfactants and the like.

For the beauty and well-cared appearance of the skin, the proportion of water in the uppermost skin layer is of greatest importance. It is possible to influence the proportion of water favorably and to a limited extent by introducing moisture regulators.

Anionic surfactants, which are in general ingredients of cleansing preparations, are capable of increasing the pH value in the horny layer in a long-lasting manner, which greatly impedes regenerative processes that serve to restore or renew the barrier function of the skin. In this instance, a new, often very unfavorable state of equilibrium develops in the horny layer between regeneration and loss of essential substances as a result of regular extraction. This state of equilibrium decisively affects the outer appearance of the skin and the physiological functioning of the horny layer.

A simple water bath alone without the addition of surfactants causes an initial swelling of the horny layer of the skin, with the degree of this swelling being dependent, e.g., on the duration of the bath and its temperature. At the same time, not only water-soluble substances, for example, water-soluble dirt particles, but also skin-inherent substances, which are responsible for the capacity of the horny layer to bind water, are rinsed off or washed away. In addition, skin-inherent, surface-active substances also cause skin fats to be separated and washed away to a certain extent. After an initial swelling, this causes a subsequent, distinct drying of the skin, which may be increased further by detergent additives.

In the case of healthy skin, these processes are in general irrelevant, since the protective mechanisms of the skin are easily capable of compensating for such slight disturbances of the upper layers of the skin. However, the protective mechanism of the skin surface becomes disrupted already in the case of nonpathological deviations from the normal state, for example, by environmentally caused damage from wear, or irritations, light damage, aged skin, etc. The protective mechanism of the skin may then possibly no longer be capable of fulfilling its function, and needs to be regenerated by external measures.

Moreover, it is known that lipid composition and lipid quantity of the horny layer of the pathologically altered, dry skin and of the dry but not yet diseased skin of younger and older people deviate from the normal condition which is found in the healthy, normally hydrated skin of a same age group. In this regard, changes in the lipid pattern of the very dry, non-eczematous skin of patients with an atopic eczema represent an extreme case of the deviations which are found in the dry skin of people with healthy skin.

In addition to cholesterol, these deviations relate quite particularly to ceramides which are greatly reduced in their quantity and, in addition, differently composed. In this regard, the deficit of ceramides 1 and 3 is particularly striking, it being known in particular in the case of ceramide 1 that it increases in a special way the order of the lipids in the intercellular membrane systems.

Disadvantageous changes in the lipid membranes of the kind described above are possibly based on a dysregulated lipid biosynthesis, and ultimately they likewise increase the transepidermal water loss. A long-lasting barrier weakness in turn makes skin that is per se healthy, more sensitive, and in individual cases may contribute to the development of eczematous processes in the diseased skin.

The effect of ointments and creams on the barrier function and hydration of the horny layer does not normally comprise a restoration or strengthening of the physico-chemical properties of the lamellae from intercellular lipids. A substantial partial effect is based on the mere covering of the treated skin regions and on the resultant water collection in the subjacent horny layer. Co-applied hygroscopic substances bind the water, so that a measurable increase of the water content in the horny layer develops. However, it is relatively easy to remove this merely physical barrier again. After the product is discontinued, the skin will return very rapidly to its condition before the start of the treatment. Moreover, the effect of skin care in the case of a regular treatment may subside, so that finally the status quo is again reached even during treatment. In the case of certain products, after their use is discontinued, the condition of the skin deteriorates, possibly temporarily. Thus, a long-lasting effect of the product is not normally achieved, or achieved only to a limited extent.

To assist the deficient skin in its natural regeneration, and to strengthen its physiological function, it has recently become more and more common to add topical preparations to the mixtures of intercellular lipids, which are to be used by the skin for rebuilding its natural barrier. However, these lipids, in particular the ceramides, are very expensive raw materials that are difficult to formulate. In addition, their effect is mostly much smaller than hoped for.

It is desirable to find ways of avoiding the disadvantages of the prior art. In particular, it is would be advantageous for the effect of skin care products to be physiological, fast, and long-lasting.

Skin care as intended by the present invention includes primarily that the natural function of the skin as a barrier against environmental influences (for example, dirt, chemicals, microorganisms) and against the loss of endogenous substances (for example, water, lipids, electrolytes) is strengthened or restored.

Products for the care, treatment, and cleansing of dry and stressed skin are known per se. However, their contribution to the regeneration of a physiologically intact, hydrated and smooth horny layer is limited in terms of scope and time.

The action of ointments and creams on the barrier function and the hydration of the horny layer is based substantially on the coverage (occlusion) of the treated skin regions. The ointment or cream represents as it were a (second) artificial barrier, which is intended to prevent a loss of water by the skin. Accordingly, this physical barrier is again easy to remove—for example, with cleansing agents—so that the original, impaired condition is reestablished. Moreover, the effect of the skin care may subside in the case of a regular treatment. After the product application is discontinued, the skin returns again very quickly to its condition before the start of the treatment. In the case of certain products, the condition of the skin sometimes even deteriorates temporarily. Thus, a long-lasting effect of the product is not achieved, or only achieved to a limited extent.

The effect of some pharmaceutical preparations on the barrier function of the skin even comprises a selective barrier damage, which is intended to make it possible for active substances to penetrate into the skin or through the skin into the body. In this regard, an impaired appearance of the skin as a side effect is partially accepted.

The effect of skin care cleansing products comprises in essence an efficient regreasing with sebum lipid-like substances. As a result of simultaneously reducing the surfactant content of such preparations, it is possible to further limit the damage to the horny layer barrier.

However, in the prior art there is a lack of preparations which positively influence the barrier function and the hydration of the horny layer, and strengthen or even restore the physico-chemical properties of the horny layer and in particular of the lamellae of intercellular lipids.

It would be advantageous to eliminate the disadvantages of the prior art. In particular, it would be advantageous to have available preparations for skin care and preparations for cleansing the skin which maintain or restore the barrier properties of the skin, particularly when the natural regeneration of the skin is insufficient. Furthermore, these preparations should be suitable for the treatment and prophylaxis of secondary damage from the drying out of the skin, for example, fissures or inflammatory or allergic processes, or even neurodermatitis. It also is desirable to have available stable, skin care cosmetic and/or dermatological agents, which protect the skin against environmental influences, such as sun and wind. In particular, it is desired that the effect of the preparation be physiological, fast, and long-lasting.

The present invention furthermore relates to preparations with extremely low so-called "stinging potential." A neurosensory phenomenon called "stinging" (sting=injure, burn, hurt) can be observed in people with sensitive, susceptible or vulnerable skin. This "sensitive skin" differs in principle from "dry skin" with thickened and hardened horny layers.

Typical reactions of "stinging" on sensitive skin are reddening, tightening and burning of the skin and itching.

Itching of atopic skin and itching with skin diseases are to be regarded as neurosensory phenomena.

"Stinging" phenomena can be regarded as disturbances that can be treated cosmetically. Severe itching, on the other hand, especially severe itching of the skin which occurs with atopy, can also be described as a more serious dermatological disorder.

Typical troublesome neurosensory phenomena associated with the terms "stinging" or "sensitive skin" are reddening of the skin, tingling, prickling, tightening and burning of the skin and itching. These phenomena can be caused by stimulating environmental conditions, for example massage, action of surfactants, the influence of weather, such as sun, cold, dryness, and also damp heat, radiant heat and UV radiation, for example from the sun.

In "Journal of the Society of Cosmetic Chemists" 28, pages 197-209 (May 1977), the entire disclosure whereof is incorporated by reference herein, P. J. Frosch and A. M. Kligman describe a method for estimating the "stinging potential" of topically administered substances. Lactic acid and pyruvic acid, for example, are employed as positives in this method. During measurement by this method, however, amino acids, in particular glycine, were also identified as substances which exert a neurosensory action (such substances are called "stingers").

According to knowledge to date, such sensitivity towards quite specific substances occurs differently in individuals. This means that a person that experiences "stinging effects" on contact with a substance will with a high probability experience it repeatedly on any further contact. However, contact with other "stingers" can just as easily proceed without any reaction.

The problem of sensitive skin affects a growing number of adults and children. Sensitive skin describes a combination of different symptoms, such as hyperreactive and intolerant skin. Atopic skin can also be included under this term. These skin conditions are often referred to by those affected, not quite correctly, as "allergic" skin. Although an allergic disorder can result in symptoms of sensitive skin, the "sensitive skin" phenomenon is not limited to allergy sufferers.

Many more or less sensitive people also suffer erythematous skin symptoms on using some deodorant or antiperspirant preparations.

Erythematous skin symptoms also occur as concomitant symptoms with certain skin diseases or irregularities. The typical skin rash with the clinical picture of acne, for example, is regularly reddened to a greater or lesser degree.

It would be advantageous to have available active substances and preparations comprising such active substances for the cosmetic and dermatological treatment and/or prophylaxis of erythematous, inflammatory, allergic or autoimmune-reactive symptoms, in particular dermatoses, and also the clinical picture of "stinging".

It would also be advantageous to have available active substances and preparations comprising such active substances which can be used for the immuno-stimulation of the skin, and here advantageously also for immuno-stimulation in the context of an action that promotes wound healing.

The present invention relates, inter alia, to cosmetic and dermatological preparations for the prophylaxis and treatment of cosmetic or dermatological skin alterations, such as, e.g., undesirable pigmentation, e.g., local hyperpigmentation and abnormal pigmentation (e.g., moles, freckles), but also for the purely cosmetic lightening of larger skin areas that are per se appropriately pigmented for the individual skin type.

Pigmentation of the skin is due to melanocytes, which are found in the bottom layer of the epidermis, the basal stratum, next to the basal cells, which—depending on skin type—are present as pigment-forming cells either individually or in relatively large numbers. Melanocytes contain melanosomes as characteristic cell organelles, which produce more melanin when stimulated by UV radiation. The melanin is transported into the keratinocytes and causes more or less pronounced brownish or brown skin coloring.

Melanin is formed as the final stage in an oxidation process, in which tyrosine, with the aid of the enzyme tyrosinase, is converted to melanin via 3,4-dihydroxyphenyl alanine (dopa), dopa-quinone, leucodopachrome, dopachrome, 5,6-dihydroxyindol and indole-5,6-quinone.

Problems with hyperpigmentation of the skin have various causes and/or are side effects of many biological processes, e.g., UV radiation (e.g. freckles, ephelides), genetic disposition, defective pigmentation of the skin and/or scarring during the healing of wounds, or skin aging (e.g. lentigines seniles).

Active substances and preparations are known which counteract skin pigmentation. Those in practical use, in addition to 8-hexadecene-1,16-dicarboxylic acid, are essentially preparations based on hydroquinone, which however on the one hand only begin to show an effect after several weeks of use while on the other hand their use over a very long period is not always safe for toxicological reasons. The inhibition of tyrosinase with substances such as koji acid, ascorbic acid, azelaic acid and their derivatives is also common, but exhibits cosmetic and dermatological disadvantages.

Another goal of skin care is to compensate for the loss by the skin of sebum and water caused by daily washing. This is particularly important if the natural regeneration ability is inadequate. Furthermore, skin care products should protect against environmental influences, in particular against sun and wind, and delay skin aging.

Chronological skin aging is caused, for example, by endogenous, genetically determined factors. The following structural damage and functional disorders, which can also fall under the term "senile xerosis", result, for example, in the epidermis and dermis as a result of aging:

a) dryness, roughness and formation of dryness wrinkles;
b) itching; and
c) reduced regreasing by sebaceous glands (e.g. after washing).

Exogenous factors, such as UV light and chemical noxae, can have a cumulative effect and, for example, accelerate or supplement the endogenous aging processes. In the epidermis and dermis, for example, the following structural damage and functional disorders appear in the skin as a result of exogenous factors; these go beyond the extent and quality of the damage in the case of chronological aging:

d) visible vascular dilation (telangiectases, couperosis);
e) flaccidity and formation of wrinkles;
f) local hyperpigmentation, hypopigmentation and abnormal pigmentation (e.g. age spots); and
g) increased susceptibility to mechanical stress (e.g. cracking).

The present invention also relates to products for the care of naturally aged skin, and to the treatment of the damage caused by photoaging, in particular of the phenomena listed under a) through g).

Products for the care of aged skin are known per se. They contain, for example, niacinamide, retinoids (vitamin A acid and/or derivatives thereof) or vitamin A and/or derivatives thereof. The extent of their effect on structural damage is, however, limited. Furthermore, in product development there are considerable difficulties in stabilizing the active ingredients to an adequate extent against oxidative decay. The use of products comprising vitamin A acid, moreover, often causes severe erythematous skin irritations. Retinoids can therefore only be used in low concentrations.

The present invention also relates to cosmetic preparations which provide effective protection against harmful oxidation processes in the skin, and also for the protection of cosmetic preparations themselves or the protection of the constituents of cosmetic preparations against harmful oxidation processes.

The present invention further relates to antioxidants, preferably those used in cosmetic or dermatological skin care preparations. In particular, the present invention also relates to cosmetic and dermatological preparations that comprise such antioxidants. In a preferred aspect, the present invention relates to cosmetic and dermatological preparations for the prophylaxis and treatment of cosmetic and dermatological skin changes, such as, for example, skin aging, in particular skin aging caused by oxidative processes.

Furthermore, the present invention relates to active substances and preparations comprising such active substances for the cosmetic and dermatological treatment or prophylaxis of erythematous, inflammatory, allergic or autoimmune-reactive symptoms, in particular dermatoses.

In a further advantageous aspect, the present invention relates to active ingredient combinations and preparations which serve for the prophylaxis and treatment of light-sensitive skin, in particular of photodermatoses.

The harmful effect of the ultraviolet part of solar radiation on the skin is generally known. Whereas rays with a wavelength of less than about 290 nm (the so-called UVC range) are absorbed by the ozone layer in the earth's atmosphere, rays in the range between about 290 nm and about 320 nm, the so-called UVB range, cause erythema, simple sunburn or even burns of greater or lesser severity. A maximum erythema activity of sunlight is indicated to occur within the relatively narrow range around 308 nm.

Numerous compounds are known for protecting against UVB radiation; these are derivatives of 3-benzylidenecamphor, of 4-aminobenzoic acid, of cinnamic acid, of salicylic acid, of benzophenone and also of 2-phenylbenzimidazole.

It is also desirable to have available filter substances for the range between about 320 nm and about 400 nm, the so-called UVA range, since the corresponding rays can cause reactions in cases of photosensitive skin. It has been found that UVA radiation results in damage of the elastic and collagenous fibers of connective tissue, which leads to premature aging of the skin, and is to be regarded as a cause of numerous phototoxic and photoallergic reactions. The harmful effect of UVB radiation can be intensified by UVA radiation.

To protect against rays of the UVA range, certain derivatives of dibenzoylmethane are therefore used. However, the photostability of these derivatives is inadequate (Int. J. Cosm. Science 10, 53 (1988), the entire disclosure whereof is incorporated by reference herein).

UV radiation can, however, also lead to photochemical reactions, in which case the photochemical reaction products interfere with the skin metabolism.

Such photochemical reaction products are predominantly free radical compounds, for example hydroxyl radicals and singlet oxygen. Undefined free radical photoproducts which form in the skin itself can also display uncontrolled secondary reactions because of their high reactivity. However, singlet oxygen, a non-free radical excited state of the oxygen molecule, can also be formed during UV irradiation, as can short-lived epoxides and many others. Singlet oxygen, for example, differs from normal triplet oxygen (free radical ground state) by virtue of its increased reactivity. However, excited, reactive (free radical) triplet states of the oxygen molecule also exist.

UV radiation is also a type of ionizing radiation. There is therefore the risk that ionic species will also form during UV exposure, which for their part are able to interfere oxidatively with the biochemical processes.

In order to prevent these reactions, additional antioxidants and/or free radical scavengers can be incorporated into cosmetic or dermatological formulations.

It has already been proposed to use vitamin E, a substance with known antioxidant action, in sunscreen formulations, although, here too, the effect achieved falls far short of expectations.

It is desirable to be able to provide cosmetically, dermatologically and pharmaceutically active substances and preparations, and sunscreen formulations which serve for the prophylaxis and treatment of photosensitive skin, in particular photodermatoses, preferably PLD.

Other names for polymorphous light dermatosis are PLD, PLE, Mallorca acne and a large number of other names, as given in the literature (e.g. A. Voelckel et al, Zentralblatt Haut- and Geschlechtskrankheiten (1989), 156, p. 2, the entire disclosure whereof is incorporated by reference herein).

Antioxidants are mainly used as substances which protect against the deterioration of the preparations in which they are present. Nevertheless, it is known that in human or animal skin undesired oxidation processes may occur as well. Such processes play an important role in skin aging.

The article "Skin Diseases Associated with Oxidative Injury" in "Oxidative Stress in Dermatology", p. 323 ff. (Marcel Decker Inc., New York, Basel, Hong Kong, Editor: Jürgen Fuchs, Frankfurt, and Lester Packer, Berkeley/Calif.), the entire disclosure whereof is incorporated by reference herein, discusses oxidative skin damage and its more direct causes.

Also for the reason of preventing such reactions, antioxidants and/or free radical scavengers can be additionally incorporated into cosmetic or dermatological formulations.

A number of antioxidants and free radical scavengers are known. For example U.S. Pat. Nos. 4,144,325 and 4,248,861, the entire disclosures whereof are incorporated by reference herein, and numerous other documents have already proposed the use of vitamin E, a substance with known antioxidant activity in sunscreen formulations, although, here, too, the effect achieved falls far short of the desired effect.

The anti-inflammatory effect of licochalcone A is known per se. To obtain this effect in topical formulations, however, the solubility of licochalcone A in the vehicle and a sufficient dermal bioavailability are important prerequisites. However, licochalcone A is a poorly soluble substance which can crystallize during storage and processing. This crystallization tendency is a great problem, since substance crystals can lead to an uncosmetic appearance, formula instabilities and/or loss of effectiveness.

It is therefore desirable to increase the solubility of licochalcone A and thus its biological availability.

It would be advantageous to find ways of avoiding the disadvantages of the prior art. In particular, the effect of eliminating the damage associated with the endogenous, chronological and exogenous aging of the skin and the prophylaxis should be lasting, sustained and without the risk of side effects.

SUMMARY OF THE INVENTION

The present invention provides an active substance combination comprising
 a. licochalcone A and/or an extract of radix glycyrrhizae inflatae that comprises licochalcone A,
 b. phenoxyethanol, and
 c. optionally, glycerin.

In one aspect of the active substance combination the weight ratio (A:B:C) is a:b:c, where a, b and c independently of one another may represent rational numbers of from about 0.001 to about 200, e.g., rational numbers of up to about 10, and
 A represents licochalcone A
 B represents phenoxyethanol
 C represents glycerin.

In another aspect, the weight ratio (B+C)/(A*100) may be from about 0.1 to about 5,000, e.g., from about 0.5 to about 1,000, or from about 1 to about 1,000.

The present invention also provides a cosmetic or dermatological preparation which comprises an effective amount of the active substance of the present invention, including the various aspects thereof as set forth above.

In one aspect, the preparation may comprise from about 0.0005% to about 50% by weight, e.g., from about 0.01% to about 20% by weight of the active substance combination, based on the total weight of the preparation.

In another aspect, the preparation may comprise from about 0.0001% to about 5% by weight, e.g., from about 0.001% to about 1% by weight, or from about 0.005% to about 0.5% by weight of licochalcone A, based on the total weight of the preparation.

In yet another aspect, the preparation may comprise from about 0.001% to about 5% by weight, e.g., from about 0.01% to about 2% by weight, or from about 0.1% to about 0.5% by weight of phenoxyethanol, based on the total weight of the preparation.

In a still further aspect, the preparation may comprise from about 0.001% to about 30% by weight, e.g., from about 0.01% to about 15% by weight, or from about 1% to about 8% by weight of glycerin, based on the total weight of the preparation.

In a still further aspect, the preparation may further comprise from about 0.001% to about 20% by weight, e.g., from about 0.01% to about 10% by weight, or from about 0.05% to about 5% by weight of one or more polyols, based on the total weight of the preparation.

The present invention further provides a cosmetic or dermatological preparation which comprises from about 0.01% to about 20% by weight, based on the total weight of the preparation, of an active substance combination comprising
(a) licochalcone A and/or an extract of radix glycyrrhizae inflatae that comprises licochalcone A,
(b) phenoxyethanol, and
(c) optionally, glycerin.

In one aspect of the preparation, the weight ratio (A:B:C) is a:b:c, where a, b and c independently of one another may represent rational numbers of from about 0.001 to about 10, and
A represents licochalcone A
B represents phenoxyethanol
C represents glycerin.

In another aspect, the weight ratio (B+C)/(A*100) may be from about 0.1 to about 1,000.

In yet another aspect, the preparation may comprise from about 0.001% to about 1% by weight, e.g., from about 0.005% to about 0.5% by weight of licochalcone A.

In a still further aspect, the preparation may comprise from about 0.01% to about 2% by weight, e.g., from about 0.1% to about 0.5% by weight of phenoxyethanol, based on the total weight of the preparation.

In a still further aspect, the preparation may comprise from about 0.001% to about 30% by weight, e.g., from about 0.01% to about 15% by weight, or from about 1% to about 8% by weight of glycerin, based on the total weight of the preparation.

In another aspect, the preparation may further comprise from about 0.001% to about 20% by weight, e.g., from about 0.01% to about 10% by weight, or from about 0.05% to about 5% by weight of one or more polyols, based on the total weight of the preparation.

The present invention also provides an emulsion which comprises the preparation of the present invention, including the various aspects thereof as set forth above.

The present invention also provides a method for the prophylaxis or treatment of inflammatory skin conditions and a method for protecting dry and sensitive skin. These methods comprise applying to at least a part of the skin the preparation of the present invention, including the various aspects thereof as set forth above.

The cosmetic or dermatological preparations according to the present invention are thoroughly satisfactory in every respect. It was not foreseeable to one of skill in the art that the preparations would lead to increased solubility and thus biological availability of licochalcone A and that the preparations would
better maintain or reestablish the barrier properties of the skin
better counteract drying out of the skin
better act against dyschromia
better act against inflammatory skin conditions
better calm sensitive skin
better alleviate reddening of the skin
better act against skin aging and
better protect the skin from environmental influences
than the preparations of the prior art.

The use of active substance combinations according to the invention or cosmetic or topical dermatological preparations with an effective content of active substance combinations according to the invention surprisingly provides not only an effective treatment, but also a prophylaxis of
deficient, sensitive, or hypoactive skin conditions or deficient, sensitive, or hypoactive conditions of skin appendages,
phenomena of premature aging of the skin (for example, wrinkles, age spots, teleangiectases) and/or of skin appendages,
environmentally caused changes (smoking, smog, reactive oxygen species, free radicals) and in particular light-induced, negative alterations of the skin and skin appendages,
light-induced skin damage,
pigmentation disorders,
sensitive, irritated and itching skin,
dry skin conditions and barrier disorders of the horny layer,
hair loss and for improved hair growth,
inflammatory skin conditions as well as atopical eczema, seborrheic eczema; polymorphous light dermatosis, psoriasis, and vitiligo.

The use of active substance combinations according to the invention or cosmetic or topical dermatological preparations with an effective amount of active substance combinations according to the invention, however, also surprisingly serves
to calm sensitive or irritated skin,
to stimulate the synthesis of collagen, hyaluronic acid and elastin,
the improved interlocking of epidermis and dermis and thus the improved elasticity and firmness of the skin
to stimulate the ceramide synthesis of the skin
to stimulate intracellular DNA synthesis, in particular in cases of deficient or hypoactive skin conditions,
to increase cell renewal and regeneration of the skin,
to increase the skin's own protective and repair mechanisms (for example, for dysfunctional enzymes, DNA, lipids, proteins),
for pre- and post-treatment in cases of topical application of laser and abrasive treatments, which serve, for example, to reduce skin wrinkles and scars, to counteract the resulting skin irritations and to promote the regeneration processes in the damaged skin.

The plant species *glycyrrhiza inflata*, like the licorice *glycyrrhiza glabra* officinal in Europe, belongs to the genus *glycyrrhiza* that belongs to the fabaceae (pea plants) plant family. The drug radix glycyrrhizae inflatae, i.e., the root of the plant, is, e.g., common in eastern medicine. The use of the drug as an anti-inflammatory agent is likewise known.

One constituent of the extract of radix glycyrrhizae inflatae is licochalcone A, which is characterized by the following structural formula:

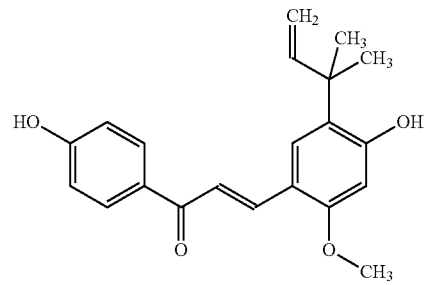 [SMILES: C=CC(C)(C)c1cc(/C=C/C(=O)c2ccc(O)cc2)c(OC)cc1O]

It is assumed that this substance, possibly in synergy with the other constituents of the extract, plays a part in the effect according to the invention.

Phenoxyethanol is characterized by the chemical structure

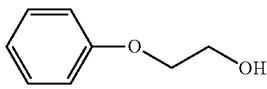

Phenoxyethanol is a viscous liquid with a light, slightly pleasant scent and an astringent taste. Phenoxyethanol is found in nature, inter alia, in tropical fruit, in *cichorium endiva* and in green tea (*camellia sinesis*). It has a mild, rose-like scent and is also used as a fixative for perfume compositions. It is miscible with acetone, ethyl alcohol and glycerin and is soluble in water and fats, e.g., olive oil and peanut oil.

Phenoxyethanol is effective above all in acidic and neutral, as well as in an alkaline media and is completely non-toxic. It provides sufficient protection already in low concentrations. Due to its good tolerability together with its excellent effectiveness it was quickly adopted in the pharmaceutical and cosmetic industry.

The use of glycerin in cosmetics is generally known. Glycerin moisturizes and smoothes the skin and is a constituent of many skin care cosmetic preparations.

According to the invention it is desirable to use glycerin. Advantageously, the preparations of the present invention contains at least about 0.001%, e.g., at least about 0.01%, at least about 0.1%, or at least about 1% by weight, but preferably not more than about 30%, e.g., not more than about 15%, or not more than about 8% by weight of glycerin, based on the total weight of the preparation.

Advantageously, a preparation according to the invention will contain at least about 0.001%, e.g., at least about 0.01%, or at least about 0.1 by weight, but preferably not more than about 2%, e.g., not more than about 1%, not more than about 0.6%, or not more than about 0.5% by weight of phenoxyethanol, based on the total weight of the preparation.

According to the invention, it is advantageous for a preparation to contain at least about 0.0001%, e.g., at least about 0.001%, at least about 0.005%, or at least about 0.01%, but not more than about 5%, e.g., not more than about 1%, or not more than about 0.5% by weight of licochalcone A, based on the total weight of the preparation.

According to the invention, it is further advantageous for the preparation to contain from about 0.001% to about 20% by weight, e.g., from about 0.01% to about 10% by weight, from about 0.05% to about 5% by weight, or from about 0.1% to about 5% by weight of one or more polyols, based on the total weight of the preparation.

Non-limiting examples of polyols which are suitable for the purposes of the invention include glycerin, butylene glycol, dipropylene glycol, propylene glycol, pentanediol, and hexanediol.

It may furthermore be advantageous for the preparations according to the present invention to contain licochalcone in the form of a constituent of a plant extract, in particular of an extract of radix glycyrrhizae inflatae.

In this regard, it may be advantageous for the cosmetic or dermatological preparations according to the invention to contain from about 0.0001% to about 10% by weight, in particular from about 0.005% to about 5% by weight, very particularly from about 0.01% to about 1% by weight of an extract of radix glycyrrhizae inflatae, based on the total weight of the preparation.

It may be particularly advantageous to start from an extract that is sold by Maruzen Co., Ltd., Japan, under the name Polyol Soluble Licorice Extract P-U.

Furthermore, it may also be advantageous to use licochalcone A in other vehicle systems, e.g., in a concentration of from about 0.0001% to about 5% by weight, in particular from about 0.001% to about 1% by weight, very particularly from about 0.003% to about 0.05% by weight.

It has proven to be very advantageous if the preparation according to the invention exhibits the following weight ratios:
(A:B:C) is selected as a:b:c, where a, b, and c represent independently of one another positive rational numbers of from about 0.001 to about 200, preferably from about 0.001 to about 10, and A, B and C represent licochalcone A, phenoxyethanol and glycerin, respectively.

Furthermore, it has proven to be advantageous to select the quotient $(B+C)/100*A$ where A, B and C are as defined above, from the range of from about 0.01 to about 5,000, preferably from the range of from about 0.1 to about 1,000.

The active substance combinations according to the present invention are used in cosmetic or dermatological compositions in concentrations of preferably at least about 0.0005%, e.g., at least about 0.01% and preferably not more than about to about 50%, e.g., not more than about 20% by weight, based on the total weight of the preparation.

The use of active substance combinations according to the invention for the prophylaxis and treatment of inflammatory skin conditions—including atopic eczema—and/or for the protection of the skin in the case of dry skin determined to be sensitive is also within the scope of the present invention.

The use of active substance combinations according to the invention for the production of cosmetic or dermatological preparations for the treatment and/or prophylaxis of pigmentation disorders is also within the scope of the present invention.

The use of active substance combinations according to the invention for the production of cosmetic or dermatological preparations for the treatment and/or prophylaxis of the symptoms of intrinsic and/or extrinsic skin aging and for the treatment and/or prophylaxis of the harmful effects of ultraviolet radiation on the skin is also within the scope of the present invention.

The use of active substance combinations according to the invention for the production of cosmetic or dermatological preparations which increase ceramide biosynthesis is also within the scope of the present invention.

The use of active substance combinations according to the invention for the production of cosmetic or dermatological preparations which strengthen the barrier function of the skin is also within the scope of the present invention.

Cosmetic or dermatological preparations according to the invention preferably contain from about 0.0001% to about 10% by weight, particularly preferably from about 0.001% to about 1% by weight, of active substance combination according to the present invention, based on the total weight of the preparations.

According to the invention, it is in particular advantageous to use active substance combinations or cosmetic or topical dermatological preparations with an effective content of active substance combinations according to the invention for the cosmetic or dermatological treatment and/or prophylaxis of undesirable skin conditions.

According to the invention, antioxidants may be present in preparations which contain active substance combinations according to the invention.

The antioxidants may advantageously be chosen from amino acids (for example glycine, histidine, tyrosine, tryptophan) and derivatives thereof, imidazoles (for example urocanic acid) and derivatives thereof, peptides, such as D,L-carnosine, D-carnosine, L-carnosine and derivatives thereof (for example anserine), carotenoids, carotenes (for example α-carotene, β-carotene, lycopene) and derivatives thereof, lipoic acid and derivatives thereof (for example, dihydrolipoic acid), aurothioglucose, propylthiouracil and other thiols (for example, thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulphoximine compounds (for example buthionine sulfoximines, homocysteine sulphoximine, buthionine sulfones, penta-, hexa- and heptathionine sulphoximines) in very low tolerated doses (for example pmol to μmol/kg), and furthermore (metal) chelating agents (for example α-hydroxy-fatty acids, palmitic acid, phytic acid, lactoferrin), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example γ-linolenic acid, linoleic acid, oleic acid), folic acid and derivatives thereof, ubiquinone and ubiquinol and derivatives thereof, vitamin C and derivatives (for example ascorbyl palmitate, Mg ascorbyl phosphate, ascorbyl acetate), vitamin B and derivatives (e.g., niacinamide), tocopherols and derivatives (for example vitamin E acetate), vitamin A and derivatives (vitamin A palmitate) and coniferyl benzoate of benzoin resin, rutic acid and derivatives thereof, ferulic acid and derivatives thereof, propyl gallate, butylated hydroxytoluene, butylated hydroxyanisole, nordihydroguaiac resin acid, nordihydroguaiaretic acid, trihydroxybutyrophenone, uric acid and derivatives thereof, mannose and derivatives thereof, zinc and derivatives thereof (for example ZnO, ZnSO$_4$), selenium and derivatives thereof (for example selenium methionine), stilbenes and derivatives thereof (for example stilbene oxide, trans-stilbene oxide) and the derivatives of these active substances mentioned which are suitable according to the invention (salts, esters, ethers, sugars, nucleotides, nucleosides, peptides and lipids).

The amount of the antioxidants (one or more compounds) in the preparations is preferably from about 0.001% to about 30% by weight, e.g., from about 0.05% to about 10% by weight, in particular from about 0.1% to about 5% by weight, based on the total weight of the preparations.

The prophylaxis or the cosmetic or dermatological treatment with the active substance combination according to the invention or with the cosmetic or topical dermatological preparations with an effective content of active substance combination according to the invention takes place in the customary manner, such that the active substance combination according to the invention or the cosmetic or topical dermatological preparations with an effective content of the active substance combination according to the invention is applied to the affected areas of the skin.

The active substance combination according to the invention can be advantageously incorporated into customary cosmetic and dermatological preparations which can be present in various forms. Thus, they can, for example, be present in the form of a solution, an emulsion of the water-in-oil (W/O) type or of the oil-in-water (O/W) type, or in the form of a multiple emulsion, for example of the water-in-oil-in-water (W/O/W) type, or the oil-in-water-in-oil (O/W/O) type, as a hydrodispersion or lipodispersion, a gel, a solid stick, or also as an aerosol.

For the purposes of the present invention, emulsions, e.g., in the form of a cream, a lotion, a foam, a cosmetic milk, are advantageous and contain, for example, fats, oils, waxes and/or other fatty substances, and also water and one or more emulsifiers, as is customarily used for this type of formulation.

It is also possible and advantageous for the purposes of the present invention, to incorporate the active substance combination according to the invention in aqueous systems or surfactant preparations for cleansing the skin and hair.

Of course, one of skill in the art will be aware that sophisticated cosmetic preparations are usually inconceivable without the customary auxiliaries and additives. The cosmetic preparations according to the invention may therefore contain cosmetic auxiliaries as are customarily used in such preparations, e.g., preservatives, bactericides, deodorants, antiperspirants, insect repellants, vitamins, antifoams, dyes, coloring pigments, thickeners, emollients, moisturizers and/or humectants, fats, oils, waxes and/or other customary constituents of a cosmetic preparation, such as alcohols, polyols, polymers, foam stabilizers, electrolytes, organic solvents and silicone derivatives.

Corresponding comments apply mutatis mutandis to the formulation of medicinal preparations.

Medicinal topical compositions for the purposes of the present invention generally comprise one or more medicaments in an effective concentration. For the sake of simplicity, for a clear distinction between cosmetic and medicinal application and corresponding products, reference is made to the legal provisions of the Federal Republic of Germany (e.g., Cosmetics Directive, Foods and Drugs Act).

Preparations according to the invention can advantageously also contain substances which absorb UV radiation in the UVB range, the total amount of the filter substances being, for example, from about 0.1% by weight to about 30% by weight, preferably from about 0.5% to about 10% by weight, in particular from about 1.0% to 6.0% by weight, based on the total weight of the preparations, in order to provide cosmetic preparations which protect the hair or the skin from the entire range of ultraviolet radiation. They can also be used as sunscreen for the hair.

Advantageous UVA filter substances for the purposes of the present invention include dibenzoylmethane derivatives, in particular 4-(tert-butyl)-4'-methoxydibenzoylmethane (CAS No. 70356-09-1), which is sold by Givaudan under the trademark Parsol® 1789 and by Merck under the trademark Eusolex® 9020.

Non-limiting examples of further advantageous UVA filter substances include hydroxybenzophenones which are characterized by the following structural formula:

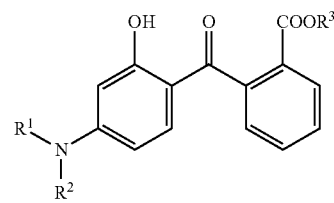

where
R$^1$ and R$^2$, independently of one another, are hydrogen, C$_1$-C$_{20}$-alkyl, C$_3$-C$_{10}$-cycloalkyl or C$_3$-C$_{10}$-cycloalkenyl, where the substituents R$^1$ and R$^2$, together with the nitrogen atom to which they are bonded, can form a 5-membered or 6-membered ring and
R$^3$ is a C$_1$-C$_{20}$-alkyl radical.

A particularly advantageous hydroxybenzophenone for the purposes of the present invention is hexyl 2-(4'-diethylamino-2'-hydroxybenzoyl)benzoate (also: aminobenzophenone), which is characterized by the following structure:

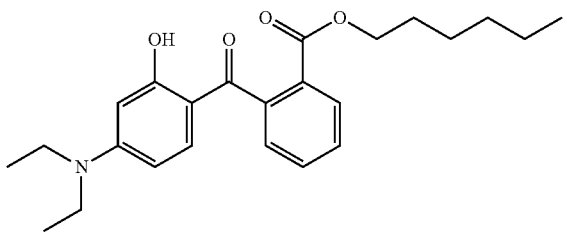 [SMILES: CCCCCCOC(=O)c1ccccc1C(=O)c1ccc(N(CC)CC)cc1O]

and is available under the trade name Uvinul A Plus from BASF.

The total amount of one or more hydroxybenzophenones in the finished cosmetic or dermatological preparations is advantageously selected from the range of from about 0.01% by weight to about 20% by weight, preferably from about 0.1% to about 10% by weight, each based on the total weight of the preparations.

Non-limiting examples of advantageous further UV filter substances in the context of the present invention include sulfonated, water-soluble UV filters, such as, e.g.,
phenylene-1,4-bis-(2-benzimidazyl)-3,3'-5,5'-tetrasulfonic acid and its salts, in particular the corresponding sodium, potassium or triethanolammonium salts, in particular phenylene-1,4-bis-(2-benzimidazyl)-3,3'-5,5'-tetrasulfonic acid bis-sodium salt with the INCI name bisimidazylate (CAS No. 180898-37-7), which is available, for example, under the trade name Neo Heliopan AP from Haarmann & Reimer;

salts of 2-phenylbenzimidazole-5-sulfonic acid, such as its sodium, potassium and triethanolammonium salts, and the sulfonic acid itself with the INCI name phenylbenzimidazole sulfonic acid (CAS No. 27503-81-7), which is available, for example, under the trade name Eusolex 232 from Merck or under the trade name Neo Heliopan Hydro from Haarmann & Reimer;

1,4-di(2-oxo-10-sulfo-3-bornylidenemethyl)-benzene (also: 3,3'-(1,4-phenylenedimethylene)-bis-(7,7-dimethyl-2-oxo-bicyclo-[2.2.1]hept-1-ylmethane sulfonic acid) and salts thereof (in particular the corresponding 10-sulfato compounds, in particular the corresponding sodium, potassium or triethanolammonium salt), which is also known as benzene-1,4-di(2-oxo-3-bornylidenemethyl-10-sulfonic acid). Benzene-1,4-di(2-oxo-3-bornylidene-methyl-10-sulfonic acid) has the INCI name terephthalidene dicamphor sulfonic acid (CAS No. 90457-82-2) and is available, for example, under the trade name Mexoryl SX from Chimex;

sulfonic acid derivatives of 3-benzylidenecamphor, such as, e.g., 4-(2-oxo-3-bornylidenemethyl)benzenesulfonic acid, 2-methyl-5-(2-oxo-3-bornylidene-methyl)-sulfonic acid and salts thereof.

Advantageous UV filter substances in the context of the present invention are furthermore so-called broad-band filters, i.e., filter substances which absorb both UVA and UVB radiation.

Advantageous broad-band filters or UVB filter substances include, for example, triazine derivatives, such as e.g.
2,4-bis-{[4-(2-ethylhexyloxy)-2-hydroxy]-phenyl}-6-(4-methoxyphenyl)-1,3,5-triazine (INCI: aniso triazine), which is available under the trade name Tinosorb® S from CIBA-Chemikalien GmbH;

Diethylhexylbutylamidotriazone (INCI: diethylhexylbutamidotriazone), which is available under the trade name UVASORB HEB from Sigma 3V;

tris(2-ethylhexyl) 4,4',4"-(1,3,5-triazine-2,4,6-triyltriimino)-tris-benzoate, also: 2,4,6-tris-[anilino-(p-carbo-2'-ethyl-1'-hexyloxy)]-1,3,5-triazine (INCI: ethylhexyl triazone), which is sold by BASF Aktiengesellschaft under the trade name UVINUL® T 150.

Another advantageous broad-band filter for the purposes of the present invention is 2,2'-methylene-bis-(6-(2H-benzotriazol-2-yl)-4-(1,1,3,3-tetramethylbutyl)-phenol) which is available under the trade name Tinosorb® M from CIBA-Chemikalien GmbH.

Another advantageous broadband filter for the purposes of the present invention is 2-(2H-benzotriazol-2-yl)-4-methyl-6-[2-methyl-3-[1,3,3,3-tetramethyl-1-[(tri-methylsilyl)oxy]-disiloxanyl]propyl]-phenol (CAS No. 155633-54-8) with the INCI name drometrizole trisiloxane, which is available under the trade name Mexoryl® XL from Chimex.

The further UV filter substances may be oil-soluble or water-soluble. Advantageous oil-soluble UVB and/or broad-band filter substances for the purposes of the present invention include, e.g.:
3-benzylidenecamphor derivatives, preferably 3-(4-methylbenzylidene)camphor, 3-benzylidenecamphor;

4-aminobenzoic acid derivatives, preferably (2-ethylhexyl) 4-(dimethylamino)-benzoate, amyl 4-(dimethylamino)benzoate;

derivatives of benzophenone, preferably 2-hydroxy-4-methoxybenzophenone, 2-hydroxy-4-methoxy-4'-methylbenzophenone, 2,2'-dihydroxy-4-methoxybenzo-phenone;

UV filters bound to polymers;
3-(4-(2,2-bisethoxycarbonylvinyl)-phenoxy)propenyl)-methoxysiloxane/-dimethylsiloxane copolymer, which is available, e.g., under the trade name Parsol® SLX from Hoffmann La Roche.

Advantageous water-soluble filter substances include, e.g., sulfonic acid derivatives of 3-benzylidenecamphor, such as, e.g., 4-(2-oxo-3-bornylidenemethyl)benzenesulfonic acid, 2-methyl-5-(2-oxo-3-bornylidenmethyl)-sulfonic acid and salts thereof.

A further light-protection filter substance which may advantageously be used according to the invention is ethylhexyl-2-cyano-3,3-diphenylacrylate (octocrylene), which is available from BASF under the name Uvinul®. N 539.

Particularly advantageous preparations for the purposes of the present invention which are characterized by a high or very high UVA and/or UVB protection furthermore preferably comprise, in addition to the filter substance(s) according to the invention, further UVA and/or broad-band filters, in particular dibenzoylmethane derivatives [for example, 4-(tert-butyl)-4'-methoxydibenzoylmethane], phenylene-1,4-bis-(2-benzimidazyl)-3,3'-5,5'-tetrasulfonic acid and salts thereof, 1,4-di(2-oxo-10-sulfo-3-bornylidenemethyl)-benzene and/or salts thereof and/or 2,4-bis-{[4-(2-ethylhexyloxy)-2-hydroxy]-phenyl}-6-(4-methoxyphenyl)-1,3,5-triazine, in each case individually or in any desired combinations with one another.

The above list of UV filters which can be employed for the purposes of the present invention is of course not intended to be limiting.

The preparations according to the invention may advantageously comprise the substances which absorb UV radiation in the UVA and/or UVB range in a total amount of, e.g., from about 0.1% by weight to about 30% by weight, preferably from about 0.5% to about 20% by weight, in particular from about 1.0% to about 15.0% by weight, in each case based on the total weight of the preparations, in order to provide cosmetic preparations which protect the hair or the skin from the entire range of ultraviolet radiation. They can also be used as sunscreens for the hair.

Cosmetic and dermatological preparations according to the invention may advantageously also contain inorganic pigments based on metal oxides and/or other metal compounds which are poorly soluble or insoluble in water, in particular oxides of titanium ($TiO_2$), zinc (ZnO), iron (e.g., $Fe_2O_3$), zirconium ($ZrO_2$), silicon ($SiO_2$), manganese (e.g., MnO), aluminum ($Al_2O_3$), cerium (e.g., $Ce_2O_3$), mixed oxides of the corresponding metals and mixtures of such oxides. Particularly preferred pigments include those based on $TiO_2$.

For the purposes of the present invention, it is particularly advantageous, although not mandatory, for the inorganic pigments to be present in hydrophobic form, i.e., to have been treated on the surface to become water-repellent. This surface treatment may involve providing the pigments with a thin hydrophobic layer by processes known per se.

One such process involves, for example, producing the hydrophobic surface layer in accordance with a reaction according to

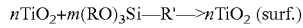

$$nTiO_2 + m(RO)_3Si\text{—}R' \longrightarrow nTiO_2 \text{ (surf.)}$$

Here, n and m are desired stoichiometric parameters, R and R' are the desired organic radicals. For example, hydrophobicized pigments prepared in accordance with DE-OS 33 14 742, the entire disclosure whereof is incorporated by reference herein, are advantageous.

Advantageous $TiO_2$ pigments are also available, for example, under the trade names MT 100 T from TAYCA, M 160 from Kemira and T 805 from Degussa.

In particular when crystalline or microcrystalline solids, for example, inorganic micropigments are to be included in the preparations of the present invention, the preparations may also contain anionic, nonionic, and/or amphoteric surfactants. Surfactants are amphophilic substances which are capable of dissolving organic, nonpolar substances in water.

The hydrophilic moieties of a surfactant molecule are in most cases polar functional groups, for example —$COO^-$, —$OSO_3^-$, —$SO_3^-$, whereas the hydrophobic parts normally represent nonpolar hydrocarbon residues. In general, surfactants are classified according to the type and charge of the hydrophilic portion of the molecule. In this regard, it is possible to distinguish between four groups:
- anionic surfactants;
- cationic surfactants;
- amphoteric surfactants; and
- nonionic surfactants.

Anionic surfactants normally comprise carboxylate, sulfate, or sulfonate groups as functional groups. In an aqueous solution, they form negatively charged, organic ions in an acidic or neutral environment. Cationic surfactants are characterized nearly exclusively by the presence of quaternary ammonium groups. In an aqueous solution, they form positively charged, organic ions in an acidic or neutral environment. Amphoteric surfactants contain both anionic and cationic groups, and accordingly in an aqueous solution act as anionic or cationic surfactants depending on the pH value. In a strongly acidic environment, they exhibit a positive charge, and in an alkaline environment they exhibit a negative charge. In the neutral pH range, however, they are zwitterionic, as demonstrated by the following example:

$RNH_2^+CH_2CH_2COOH\ X^-$ (at pH=2) $X^-$=any desired anion, e.g., $Cl^-$
$RNH_2^+CH_2CH_2COO^-$ (at pH=7)
$RNHCH_2CH_2COO^-\ B^+$ (at pH=12) $B^+$=any desired cation, e.g., $Na^+$ Typical of nonionic surfactants are polyether chains. Nonionic surfactants do not form ions in an aqueous medium.

A. Anionic Surfactants

Non-limiting examples of anionic surfactants that may advantageously be used for the purposes of the present invention include Acylamino acids (and salts thereof), such as:
1. Acyl glutamate, for example, sodium acyl glutamate, di-TEA-palmitoyl aspartate, and sodium caprylic/capric glutamate;
2. Acylpeptides, for example, palmitoyl-hydrolyzed milk protein, sodium cocoyl-hydrolyzed soy protein, and sodium/potassium cocoyl-hydrolyzed collagen;
3. Sarcosinates, for example, myristoyl sarcosin, TEA-lauroyl sarcosinate, sodium lauroyl sarcosinate, and sodium cocoyl sarcosinate;
4. Taurates, for example, sodium lauroyl taurate and sodium methylcocoyl taurate;
5. Acyl lactylates, lauroyl lactylate, caproyl lactylate
6. Alaninates.

Carboxylic acids and derivatives, such as:
1. Carboxylic acids, for example, lauric acid, aluminum stearate, magnesium alkanolate, and zinc undecylenate;
2. Ester carboxylic acids, for example, calcium stearoyl lactylate, laureth-6 citrate, and sodium PEG-4 lauramide carboxylate;
3. Ether carboxylic acids, for example, sodium laureth-13 carboxylate, and sodium PEG-6 cocoamide carboxylate Esters of phosphoric acid and salts, such as, for example, DEA-oleth-10-phosphate and dilaureth-4 phosphate, Sulfonic acids and salts, such as:
1. Acyl isethionate, for example, sodium-ammoniumcocoyl isethionate;
2. Alkyaryl sulfonates;
3. Alkyl sulfonates, for example, sodium coco monoglyceride sulfate, sodium $C_{12-14}$ olefin sulfonate, sodium lauryl sulfoacetate, and magnesium PEG-3 cocamide sulfate;
4. Sulfosuccinates, for example, dioctyl sodium sulfosuccinate, disodium laureth sulfosuccinate, disodium lauryl sulfosuccinate, and disodium undecylenamido-MEA-sulfosuccinate;

and

Esters of sulfuric acid, such as:
1. Alkyl ether sulfates, for example, sodium, ammonium, magnesium, MIPA, TIPA, laureth sulfate, sodium myreth sulfate, and sodium $C_{12-13}$ pareth sulfate; and
2. Alkyl sulfates, for example, sodium, ammonium, and TEA-lauryl sulfate.

B. Cationic Surfactants

Non-limiting examples of cationic surfactants that may advantageously be used include
1. Alkylamines,
2. Alkylimidazoles,
3. Ethoxylated amines, and
4. Quaternary surfactants
5. Esterquats.

Quaternary surfactants contain at least one nitrogen atom, which is covalently bonded to 4 alkyl or aryl groups. Irrespective of the pH value, this results in a positive charge. Advantageous are alkylbetaine, alkylamidopropylbetaine, and alkylamidopropyl-hydroxysulfaine. The cationic surfactants that may be used in accordance with the invention can also be selected from quaternary ammonium compounds, in particular benzyltrialkyl ammoniumchlorides or bromides, such as, for example, benzyldimethylstearyl ammonium chloride, furthermore alkyltrialkyl ammonium salts, for example, cetyltrimethyl ammonium chloride or bromide, alkyldimethylhydroxyethyl ammonium chloride or bromide, dialkyldimethyl ammonium chloride or bromide, alkylamide ethyltrimethylammonium ether sulfates, alkylpyridinium salts, for example, lauryl or cetyl pyrimidinium chloride, imidazoline derivatives and compounds having cationic character, such as amine oxides, for example, alkyldimethylamine oxides or alkylaminoethyl dimethylamine oxides. The use of cetyltrimethyl ammonium salts is particularly advantageous.

C. Amphoteric Surfactants

Non-limiting examples of amphoteric surfactants that may advantageously be used include
1. Acyl-/dialkyl ethylenediamine, for example, sodium acyl amphoacetate, disodiumacyl amphodipropionate, disodium alkyl amphodiacetate, sodium acylamphohydroxypropyl sulfonate, disodium acyl amphodiacetate, and sodium acyl amphopropionate;
2. N-alkylamino acids, for example, aminopropyl alkylglutamide, alkylaminopropionic acid, sodium alkylimidodipropionate and lauroamphocarboxyglycinate.

D. Nonionic Surfactants

Non-limiting examples of nonionic surfactants which may advantageously be used include
1. Alcohols;
2. Alkanolamides, such as MEA/DEA/MIPA cocoamides;
3. Amine oxides, such as cocoamidopropylamine oxide;
4. Esters, which result from the esterification of carboxylic acids with ethylene oxide, glycerin, sorbitan, or other alcohols;
5. Ethers, for example, ethoxylated/propoxylated alcohols, ethoxylated/propoxylated esters, ethoxylated/propoxylated glycerol esters, ethoxylated/propoxylated cholesterols, ethoxylated/propoxylated triglyceride esters, ethoxylated/-propoxylated lanolin, ethoxylated/propoxylated polysiloxanes, propoxylated POE-ethers, and alkyl polyglycosides, such as lauryl glucoside, decyl glycoside and coco glycoside;
6. Sucrose esters, sucrose ethers;
7. Polyglycerol esters, diglycerol esters, monoglycerol esters;
8. Methylglucose esters, esters of hydroxy acids.

It may also be advantageous to use a combination of anionic and/or amphoteric surfactants with one or more nonionic surfactants.

In the preparations according to the invention, the surface-active substance may, for example, be present in a concentration of from about 1% to about 95% by weight, based on the total weight of the preparations.

The lipid phase of cosmetic or dermatological emulsions according to the invention may advantageously be selected from the following group of substances:
mineral oils, mineral waxes;
oils, such as triglycerides of capric or caprylic acids, dialkyl ether and dialkyl carbonates, such as, e.g., dicaprylyl ether or dicaprylyl carbonate; furthermore natural oils, such as, e.g., castor oil;
fats, waxes, and other natural and synthetic lipoids, preferably esters of fatty acids with alcohols having a low carbon number, e.g., with isopropanol, propylene glycol or glycerol, or esters of fatty alcohols with alkanoic acids of a low carbon number or with fatty acids;
alkylbenzoates;
silicone oils, such as dimethylpolysiloxanes, diethylpolysiloxanes, diphenylpolysiloxanes, as well as mixed forms thereof.

Advantageously, the oil phase of the emulsions of the present invention may further be selected from esters of saturated and/or unsaturated, branched and/or unbranched alkane carboxylic acids having a chain length of from 3 to about 30 carbon atoms and saturated and/or unsaturated, branched and/or unbranched alcohols having a chain length of from 3 to about 30 carbon atoms; from esters of aromatic carboxylic acids and saturated and/or unsaturated, branched and/or unbranched alcohols having a chain length of from 3 to about 30 carbon atoms. By way of non-limiting example, such ester oils may advantageously be selected from isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate, as well as synthetic, semisynthetic, and natural mixtures of such esters, for example, jojoba oil.

Furthermore, the oil phase may advantageously be selected from branched and unbranched hydrocarbons and hydrocarbon waxes, silicone oils, dialkyl ethers, saturated and/or unsaturated, branched and/or unbranched alcohols, as well as fatty acid triglycerides, namely the triglycerol esters of saturated and/or unsaturated, branched and/or unbranched alkane carboxylic acids having a chain length of from about 8 to about 24, in particular from about 12 to about 18 carbon atoms. The fatty acid triglycerides may advantageously be selected, for example, from synthetic, semisynthetic and natural oils, for example, olive oil, sunflower seed oil, soy oil, peanut oil, rape oil, almond oil, palm oil, coconut oil, palm kernel oil, and the like.

Any mixtures of such oil and wax components may also be used advantageously for the purposes of the present invention. In some instances, it may also be advantageous to use waxes, for example, cetyl palmitate, as the only lipid component of the oil phase.

Advantageously, the oil phase may also be selected from 2-ethylhexyl stearate, octyldodecanol, isotridecyl isononanoate, isoeicosane, 2-ethylhexyl cocoate, $C_{12-15}$-alkyl benzoate, triglycerides of caprylic/capric acid, dicaprylyl ether and dicaprylyl carbonate.

Particularly advantageous are mixtures of $C_{12-15}$ alkyl benzoate and 2-ethylhexyl isostearate, mixtures of $C_{12-15}$ alkyl benzoate and isotridecyl isononanoate, as well as mixtures of $C_{12-15}$ alkyl benzoate, 2-ethylhexyl isostearate and isotridecyl isononanoate.

Non-limiting examples of hydrocarbons that may advantageously be used for the purposes of the invention include paraffin oil, squalane and squalene.

The oil phase may advantageously also contain cyclic and/or linear silicone oils, or be composed entirely of such oils, although it is preferable to use an additional content of other oil phase components apart from the silicone oil(s). Such silicones or silicone oils may be in the form of monomers, which are generally characterized by the following structural elements:

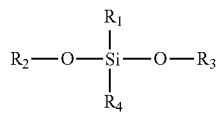

Linear silicones having two or more siloxyl units, which may be used advantageously according to the present invention, are generally characterized by the following structural elements:

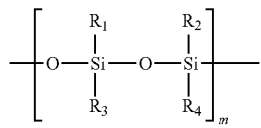

where the silicon atoms can be substituted with identical or different alkyl radicals and/or aryl radicals, which are shown here in general terms by the radicals $R_1$-$R_4$ (that is to say the number of different radicals is not necessarily limited to up to 4). m will usually assume values of from about 2 to about 200,000.

Cyclic silicones which may be used advantageously according to the invention are generally characterized by the following structural elements:

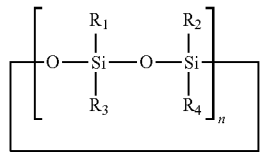

where the silicon atoms can be substituted with identical or different alkyl radicals and/or aryl radicals, which are shown here in general terms by the radicals $R_1$-$R_4$ (that is to say the number of different radicals is not necessarily limited to up to 4). n will usually assume values of from 3/2 to about 20. Fractions for n take into consideration the fact that uneven numbers of siloxyl groups may be present in the ring.

Advantageously, cyclomethicone (e.g., decamethylcyclopentasiloxane) may be used as the silicone oil for use in the present invention. However, other silicone oils can also be used advantageously for the purposes of the present invention, for example, undecamethylcyclotrisiloxane, polydimethylsiloxane, poly(methylphenylsiloxane), cetyldimethicone, and behenoxydimethicone.

Also advantageous are mixtures of cyclomethicone and isotridecyl isononanoate, and mixtures of cyclomethicone and 2-ethylhexyl isostearate.

It may, however, also be advantageous to select silicone oils of similar constitution to the above-described compounds whose organic side chains are derivatized, for example, polyethoxylated and/or polypropoxylated. These include, for example, polysiloxane-polyalkyl-polyether copolymers, such as cetyl-dimethicone copolyol, and (cetyl-dimethicone copolyol (and) polyglyceryl-4-isostearate (and) hexyl laurate).

Also particularly advantageous are mixtures of cyclomethicone and isotridecyl isononanoate, and of cyclomethicone and 2-ethylhexyl isostearate.

Advantageously, the aqueous phase of the preparations according to the invention may optionally comprise alcohols, diols or polyols of low carbon number, and ethers thereof, preferably ethanol, isopropanol, propylene glycol, glycerin, ethylhexylglycerin, ethylene glycol, ethylene glycol monoethyl or monobutyl ether, propylene glycol monomethyl, monoethyl or monobutyl ether, diethylene glycol monomethyl or monoethyl ether and analogous products, and also, in particular, one or more thickeners which can advantageously be chosen from silicon dioxide and aluminum silicates.

Preparations according to the invention which are present in the form of emulsions may advantageously comprise, in particular, one or more hydrocolloids. These hydrocolloids may advantageously be chosen from gums, polysaccharides, cellulose derivatives, phyllosilicates, polyacrylates and/or other polymers.

Preparations according to the invention which are present in the form of hydrogels may contain one or more hydrocolloids. These hydorcolloids may advantageously be selected, for example, from the above-mentioned group of thickeners.

The gums include saps from plants or trees which harden in the air and form resins, and extracts from aquatic plants. From this group, gum arabic, carob flour, tragacanth, karaya, guar gum, pectin, gellan gum, carrageen, agar, algins, chondrus, xanthan gum may, for example, be chosen advantageously for the purposes of the present invention.

Also advantageous is the use of derivatized gums, such as, for example, hydroxypropyl guar (Jaguar® HP 8).

Non-limiting examples of suitable polysaccharides and polysaccharide derivatives include hyaluronic acid, chitin and chitosan, chondroitin sulfates, starch and starch derivatives.

Suitable cellulose derivatives include, for example, methylcellulose, carboxymethylcellulose, hydroxyethylcellulose, and hydroxypropylmethylcellulose.

The phyllosilicates include naturally occurring and synthetic clays, such as, for example, montmorillonite, bentonite, hectorite, laponite, magnesium aluminum silicates such as Veegum®. These can be used as such or in modified form, such as, for example, stearylalkonium hectorites.

In addition, silica gels can also be used advantageously for the purposes of the present invention.

The polyacrylates include, for example, Carbopol grades from Goodrich (Carbopol 980, 981, 1382, 5984, 2984, EDT 2001 or Pemulen TR2).

The polymers include, for example, polyacrylamides (Seppigel 305), polyvinyl alcohols, PVP, PVP/VA copolymers, polyglycols, and ammoniumpolyacryloyldimethyltaurates and ammoniumacryloyldimethyltaurate/-vinylpyrrolidone copolymers.

Preparations according to the invention in the form of emulsions may comprise one or more emulsifiers. These emulsifiers may advantageously be chosen from nonionic, anionic, cationic and amphoteric emulsifiers.

Non-limiting examples of nonionic emulsifiers include
a) partial fatty acid esters and fatty acid esters of polyhydric alcohols and ethoxylated derivatives thereof (e.g., glyceryl monostearates, sorbitan stearates, glyceryl stearyl citrates, sucrose stearates), b) ethoxylated fatty alcohols and fatty acids,
c) ethoxylated fatty amines, fatty acid amides, fatty acid alkanolamides,
d) alkylphenol polyglycol ethers (e.g., Triton X).

Non-limiting examples of anionic emulsifiers include
a) soaps (e.g., sodium stearate),
b) fatty alcohol sulfates,
c) mono-, di- and trialkylphosphoric esters and ethoxylates thereof.

Non-limiting examples of cationic emulsifiers include
a) quaternary ammonium compounds with a long-chain aliphatic radical, e.g., distearyidiammonium chloride Non-limiting examples of amphoteric emulsifiers include
a) alkylaminoalkanecarboxylic acids,
b) betaines, sulfobetaines
c) imidazoline derivatives In addition, there are naturally occurring emulsifiers, which include beeswax, wool wax, lecithin and sterols.

Non-limiting examples of advantageous O/W emulsifiers include polyethoxylated or polypropoxylated or polyethoxylated and polypropoxylated products, for example:
  fatty alcohol ethoxylates;
  ethoxylated wool wax alcohols;
  polyethylene glycol ethers of the general formula R—O—(—CH$_2$—CH$_2$—O—)$_n$—R';
  fatty acid ethoxylates of the general formula R—COO—(—CH$_2$—CH$_2$—O—)$_n$—H;
  etherified fatty acid ethoxylates of the general formula R—COO—(—CH$_2$—CH$_2$—O—)$_n$—R';
  esterified fatty acid ethoxylates of the general formula R—COO—(—CH$_2$—CH$_2$—O—)$_n$—C(O)—R';
  fatty acid esters of polyethyleneglycol glycerin;
  ethoxylated sorbitan esters;
  cholesterol ethoxylates;
  ethoxylated triglycerides
  alkyl ether carboxylic acids of the general formula R—O—(—CH$_2$—CH$_2$—O—)$_n$—CH$_2$—COOH where n is a number of from about 5 to about 30;
  fatty acid esters of polyoxyethylene sorbitol;
  alkylether sulfates of the general formula R—O—(—CH$_2$—CH$_2$—O—)$_n$—SO$_3$—H;
  fatty alcohol propoxylates of the general formula R—O—(—CH$_2$—CH(CH$_3$)—O—)$_n$—H;
  polypropylene glycol ethers of the general formula R—O—(—CH$_2$—CH(CH$_3$)—O—)$_n$—R';
  propoxylated wool wax alcohols;
  etherified fatty acid propoxylates R—COO—(—CH$_2$—CH(CH$_3$)—O—)$_n$—R';
  esterified fatty acid propoxylates of the general formula R—COO—(—CH$_2$—CH(CH$_3$)—O—)$_n$—C(O)—R';
  fatty acid propoxylates of the general formula R—COO—(—CH$_2$—CH(CH$_3$)—O—)$_n$—H;
  fatty acid esters of polypropylene glycolglycerin
  propoxylated sorbitan esters;
  cholesterol propoxylates
  propoxylated triglycerides;
  alkyl ether carboxylic acids of the general formula R—O—(—CH$_2$—CH(CH$_3$)O—)$_n$—CH$_2$—COOH;
  alkylether sulfates or the parent acids of these sulfates of the general formula R—O—(—CH$_2$—CH(CH$_3$)—O—)$_n$—SO$_3$—H;
  fatty alcohol ethoxylates/propoxylates of the general formula R—O—X$_n$—Y$_m$—H;
  polypropylene glycol ethers of the general formula R—O—X$_n$—Y$_m$—R';
  etherified fatty acid propoxylates of the general formula R—COO—X$_n$—Y$_m$—R;
  fatty acid ethoxylates/propoxylates of the general formula R—COO—X$_n$—Y$_m$—H.

If the O/W emulsifiers comprise saturated radicals R and R' it is particularly advantageous to select the polyethoxylated or polypropoxylated or polyethoxylated and polypropoxylated O/W emulsifiers from substances with HLB values of from about 11 to about 18, e.g., from about 14.5 to about 15.5. If the O/W emulsifiers comprise unsaturated radicals R and/or R', or if isoalkyl derivatives are present, the preferred HLB values of such emulsifiers can also be lower or higher than the indicated values.

It may be advantageous to select the fatty alcohol ethoxylates from ethoxylated stearyl alcohols, cetyl alcohols and cetyl stearyl alcohols (cetearyl alcohols). Especially preferred fatty alcohol ethoxylates include:
  polyethylene glycol(13)stearyl ether (steareth-13), polyethylene glycol(14)stearyl ether (steareth-14), polyethylene glycol(15)stearyl ether (steareth-15), polyethylene glycol(16)stearyl ether (steareth-16), polyethylene glycol(17)stearyl ether (steareth-17), polyethylene glycol(18)stearyl ether (steareth-18), polyethylene glycol(19)stearyl ether (steareth-19), polyethylene glycol(20)stearyl ether (steareth-20),
  polyethylene glycol(12)isostearyl ether (isosteareth-12), polyethylene glycol(13)isostearyl ether (isosteareth-13), polyethylene glycol(14)isostearyl ether (isosteareth-14), polyethylene glycol(15)isostearyl ether (isosteareth-15), polyethylene glycol(16)isostearyl ether (isosteareth-16), polyethylene glycol(17)isostearyl ether (isosteareth-17), polyethylene glycol(18)isostearyl ether (isosteareth-18), polyethylene glycol(19)isostearyl ether (isosteareth-19), polyethylene glycol(20)isostearyl ether (isosteareth-20);
  polyethylene glycol(13)cetyl ether (ceteth-13), polyethylene glycol(14)cetyl ether (ceteth-14), polyethylene glycol(15)cetyl ether (ceteth-15), polyethylene glycol(16)cetyl ether (ceteth-16), polyethylene glycol(17)cetyl ether (ceteth-17), polyethylene glycol(18)cetyl ether (ceteth-18), polyethylene glycol(19)cetyl ether (ceteth-19), polyethylene glycol(20)cetyl ether (ceteth-20);
  polyethylene glycol (13)isocetyl ether (isoceteth-13), polyethylene glycol (14)isocetyl ether (isoceteth-14), polyethylene glycol (15)isocetyl ether (isoceteth-15), polyethylene glycol (16)isocetyl ether (isoceteth-16), polyethylene glycol (17)isocetyl ether (isoceteth-17), polyethylene glycol (18)isocetyl ether (isoceteth-18), polyethylene glycol(19) isocetyl ether (isoceteth-19), polyethylene glycol(20)isocetyl ether (isoceteth-20);
  polyethylene glycol(12)oleyl ether (oleth-12), polyethylene glycol(13)oleyl ether (oleth-13), polyethylene glycol (14)oleyl ether (oleth-14), polyethylene glycol(15)oleyl ether (oleth-15);
  polyethylene glycol(12)lauryl ether (laureth-12), polyethylene glycol(12)isolauryl ether (isolaureth-12);
  polyethylene glycol(13)cetylstearyl ether (ceteareth-13), polyethylene glycol(14)cetylstearyl ether (ceteareth-14), polyethylene glycol(15)cetylstearyl ether (ceteareth-15), polyethylene glycol(16)cetylstearyl ether (ceteareth-16), polyethylene glycol(17)cetylstearyl ether (ceteareth-17), polyethylene glycol(18)cetylstearyl ether (ceteareth-18), polyethylene glycol(19)cetylstearyl ether (ceteareth-19), polyethylene glycol(20)cetylstearyl ether (ceteareth-20).

It may also be advantageous to select the fatty acid ethoxylates from the following group:
  polyethylene glycol(20) stearate, polyethylene glycol(21) stearate, polyethylene glycol(22) stearate, polyethylene glycol(23) stearate, polyethylene glycol(24) stearate, polyethylene glycol(25) stearate;

polyethylene glycol(12)isostearate, polyethylene glycol(13)isostearate, polyethylene glycol(14)isostearate, polyethylene glycol(15)isostearate, polyethylene glycol(16)isostearate, polyethylene glycol(17)isostearate, polyethylene glycol(18) isostearate, polyethylene glycol(19)isostearate, polyethylene glycol(20)isostearate, polyethylene glycol(21) isostearate, polyethylene glycol(22)isostearate, polyethylene glycol(23)isostearate, polyethylene glycol(24)isostearate, polyethylene glycol(25) isostearate;

polyethylene glycol(12)oleate, polyethylene glycol(13) oleate, polyethylene glycol(14)oleate, polyethylene glycol(15)oleate, polyethylene glycol(16)oleate, polyethylene glycol(17)oleate, polyethylene glycol(18)oleate, polyethylene glycol(19) oleate, polyethylene glycol(20)oleate.

Sodium laureth-11-carboxylate may advantageously be used as an ethoxylated alkyl ether carboxylic acid salt.

Sodium laureth 1-4 sulfate may advantageously be used as an alkyl ether sulfate.

Polyethylene glycol(30)cholesteryl ether may advantageously be used as an ethoxylated cholesterol derivative. Polyethylene glycol(25)soyasterol has also proven advantageous.

Polyethylene glycol(60) evening primrose glycerides may advantageously be used as ethoxylated triglycerides.

It may also be advantageous to select the fatty acid esters of polyethylene glycol glycerol from polyethylene glycol (20)glyceryl laurate, polyethylene glycol(21)glyceryl laurate, polyethylene glycol(22)glyceryl laurate, polyethylene glycol(23)glyceryl laurate, polyethylene glycol(6)glyceryl caprate/caprinate, polyethylene glycol(20)glyceryl oleate, polyethylene glycol(20)glyceryl isostearate, and polyethylene glycol(18)glyceryl oleate/cocoate.

It may likewise be advantageous to select the sorbitan esters from polyethylene glycol(20)sorbitan monolaurate, polyethylene glycol(20)sorbitan monostearate, polyethylene glycol(20)sorbitan monoisostearate, polyethylene glycol (20)sorbitan monopalmitate, and polyethylene glycol(20) sorbitan monooleate.

It may also be advantageous to use as W/O emulsifiers fatty alcohols having from about 8 to about 30 carbon atoms, monoglycerol esters of saturated and/or unsaturated, branched and/or unbranched alkanecarboxylic acids having a chain length of from about 8 to about 24, in particular from about 12 to about 18 carbon atoms, diglycerol esters of saturated and/or unsaturated, branched and/or unbranched alkane-carboxylic acids having a chain length of from about 8 to about 24, in particular from about 12 to about 18 carbon atoms, monoglycerol ethers of saturated and/or unsaturated, branched and/or unbranched alcohols having a chain length of from about 8 to about 24, in particular from about 12 to about 18 carbon atoms, diglycerol ethers of saturated and/or unsaturated, branched and/or unbranched alcohols having a chain length of from about 8 to about 24, in particular from about 12 to about 18 carbon atoms, propylene glycol esters of saturated and/or unsaturated, branched and/or unbranched alkane carboxylic acids having a chain length of from about 8 to about 24, in particular from about 12 to about 18 carbon atoms, as well as sorbitan esters of saturated and/or unsaturated, branched and/or unbranched alkane carboxylic acids having a chain length of from about 8 to about 24, in particular from about 12 to about 18 carbon atoms.

Non-limiting examples of particularly advantageous W/O emulsifiers include glyceryl monostearate, glyceryl monoisostearate, glyceryl monomyristate, glyceryl monooleate, diglyceryl monostearate, diglyceryl monoisostearate, propylene glycol monostearate, propylene glycol monoisostearate, propylene glycol monocaprylate, propylene glycol monolaurate, sorbitan monoisostearate, sorbitan monolaurate, sorbitan monocaprylate, sorbitan monoisooleate, sucrose distearate, cetyl alcohol, stearyl alcohol, arachidyl alcohol, behenyl alcohol, isobehenyl alcohol, selachyl alcohol, chimyl alcohol, polyethylene glycol (2)stearyl ether (steareth-2), glyceryl monolaurate, glyceryl monocaprinate, glyceryl monocaprylate.

DETAILED DESCRIPTION OF THE PRESENT INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description making apparent to those skilled in the art how the several forms of the present invention may be embodied in practice. Unless stated otherwise, all amounts, fractions and percentages given are based on the weight and the total amount or on the total weight of the preparations.

Example 1

| O/W Night Cream | % by weight |
|---|---|
| Glyceryl stearate citrate | 2 |
| Shea butter | 2 |
| Stearyl alcohol | 2 |
| Cetyl alcohol | 2 |
| Hydrogenated coco glycerides | 2 |
| Caprylic acid/capric acid triglyceride | 2 |
| Ethylhexyl cocoate ester | 2 |
| Cyclomethicone | 3 |
| Dicaprylyl ether | 2 |
| Tocopherylacetate | 1 |
| Sodium ascorbylphosphate | 0.1 |
| Licochalcone A | 0.01 |
| Retinyl palmitate | 0.1 |
| Phenoxyethanol | 0.6 |
| p-Hydroxybenzoic acid alkyl ester (paraben) | 0.6 |
| Ethylhexylglycerin | 0.5 |
| Polyacrylic acid (Carbomer) | 0.1 |
| EDTA | 0.2 |
| Glycerin | 10 |
| Water-soluble and/or oil-soluble dyes | 0.05 |
| Fillers/additives (SiO$_2$, BHT) | 0.2 |
| Perfume | q.s. |
| Water | ad 100 |

Example 2
Cream

| | % by weight |
|---|---|
| Glyceryl stearate, self-emulsifying | 5 |
| Stearyl alcohol | 1 |
| Shea butter | 1 |
| C$_{12-15}$ Alkyl benzoate | 3 |
| Caprylic acid/capric acid triglycerides | 2 |
| Mineral oil | 1 |
| Dicaprylyl carbonate | 3 |
| Ethylhexyl cyanodiphenylacrylate (octocrylene) | 5 |
| Ethylhexyl triazone | 1 |
| Bis-ethylhexyloxyphenol-methoxyphenyl triazine | 1 |
| Citric acid, sodium salt | 0.1 |
| Licochalcone A | 0.05 |

Example 2
Cream

| | % by weight |
|---|---|
| Phenoxyethanol | 0.6 |
| p-Hydroxybenzoic acid alkyl ester (paraben) | 0.3 |
| Hexamidine diisethionate | 0.04 |
| 1,3-Dimethylol-5,5-dimethyl-hydantoin(DMDM hydantoin) | 0.1 |
| EDTA | 0.2 |
| Ethanol (denaturated) | 2 |
| Ammoniumacryloyldimethyltaurate/vinylpyrrolidone copolymers | 0.5 |
| Glycerin | 10 |
| Butyleneglycol | 1 |
| Additives (distarch phosphate, $SiO_2$, BHT) | 1 |
| Perfume | q.s. |
| Water | ad 100 |

Example 3
Sunscreen Cream

| | % by weight |
|---|---|
| Glyceryl stearate | 3 |
| PEG-40-stearate | 1 |
| Cetearyl alcohol | 3 |
| Shea butter | 2 |
| $C_{12-15}$ Alkyl benzoate | 2 |
| Coco glycerides | 2 |
| Octyldodecanol | 3 |
| Beeswax | 1 |
| Cholesterol | 0.4 |
| Ethylhexyl methoxycinnamate | 5 |
| Phenylbenzimidazole sulfonic acid | 2 |
| Butyl methoxydibenzoylmethane | 2 |
| Ubiquinone (Q 10) | 0.03 |
| Sodium ascorbylphosphate | 0.1 |
| Tocopheryl acetate | 1 |
| Licochalcone A | 0.1 |
| Methylpropanediol | 1 |
| Phenoxyethanol | 0.5 |
| p-Hydroxybenzoic acid alkyl ester (paraben) | 0.2 |
| Diazolidinylurea | 0.1 |
| Carbomer | 0.1 |
| Carrageenan | 0.1 |
| Glycerin | 7 |
| Additives (BHT, iminodisuccinate) | 0.4 |
| Perfume | q.s. |
| Water | ad 100 |

Example 4
Cream

| | % by weight |
|---|---|
| Glyceryl stearate | 1 |
| Stearic acid | 3 |
| Stearyl alcohol | 2 |
| Cetyl alcohol | 2 |
| $C_{12-15}$ Alkyl benzoate | 2 |
| Caprylic acid/capric acid triglycerides | 2 |
| Macadamia oil | 1 |
| Myristy Imyristates | 2 |
| Dimethicone | 2 |
| Hydrogenated coco glycerides | 1 |
| Ethylhexylglycerin | 0.5 |
| Tocopheryl acetate | 1 |
| Licochalcone A | 0.01 |
| Creatine | 0.1 |
| Ubiquinone (Q10) | 0.03 |
| Phenoxyethanol | 0.4 |
| p-Hydroxybenzoic acid alkyl ester (paraben) | 0.3 |

Example 4
Cream

| | % by weight |
|---|---|
| Iodopropynylbutylcarbamate | 0.02 |
| Cyclodextrin | 0.3 |
| Iminodisuccinate | 0.2 |
| Carbomer | 0.3 |
| Glycerin | 5 |
| Butylene glycol | 1 |
| Methylpropanediol | 1 |
| Additives ($SiO_2$, talc) | 0.5 |
| Perfume | q.s. |
| Water | ad 100 |

Example 5
After Sun Gel

| | % by weight |
|---|---|
| Cetyl alcohol | 2 |
| Shea butter | 1 |
| Caprylic acid/capric acid triglyceride | 2 |
| Octyldodecanol | 1 |
| Dicaprylyl carbonate | 5 |
| Dimethicone | 2 |
| Polydecene | 2 |
| Methyl palmitate | 3 |
| Licochalcone A | 0.02 |
| Sodium ascorbylphosphate | 0.05 |
| Iminodisuccinate | 0.2 |
| Ethanol | |
| Phenoxyethanol | 0.3 |
| p-Hydroxybenzoic acid alkyl ester (paraben) | 0.4 |
| Alkylacrylate crosspolymer | 0.2 |
| Glycerin | 5 |
| Perfume | q.s. |
| Water | ad 100 |

Example 6
After Shave Gel

| | % by weight |
|---|---|
| Triceteareth-4-phosphate | 0.5 |
| Cyclomethicone | 2.0 |
| Octyldodecanol | 1.0 |
| Dicaprylyl carbonate | 3.0 |
| Methyl palmitate | 2.0 |
| Licochalcone A | 0.02 |
| Allantoin | 0.1 |
| Tocopheryl acetate | 0.5 |
| Iminodisuccinate | 0.2 |
| Ethanol | 5.0 |
| Phenoxyethanol | 0.5 |
| p-Hydroxybenzoic acid alkyl ester (paraben) | 0.4 |
| Alkylacrylate crosspolymer | 0.3 |
| Distarch phosphate | 1.0 |
| Butylene glycol | 3.0 |
| Iminodisuccinate | 0.2 |
| Glycerin | 4.0 |
| Perfume | q.s. |
| Water | ad 100 |

Example 7
O/W Cream

| | % by weight |
|---|---|
| Glyceryl stearate | 2.5 |
| PEG-40-stearate | 1 |
| Cetearyl alcohol | 2 |
| Hydrogenated coco glycerides | 1 |
| Myristyl myristate | 2 |
| $C_{12-15}$ Alkyl benzoate | 4 |
| Caprylic acid/capric acid triglycerides | 2 |
| Octyldodecanol | 1 |
| Dicaprylyl carbonate | 3 |
| Ethylhexyl cyanodiphenylacrylate (octocrylene) | 5 |
| 2-Hydroxy-4-methoxy-benzophenone (oxybenzone) | 3 |
| Ubiquinone (Q10) | 0.03 |
| Licochalcone A | 0.005 |
| alpha-Glucosylrutin | 0.1 |
| Ceramide III | 0.1 |
| Phenoxyethanol | 0.5 |
| p-Hydroxybenzoic acid alkyl ester (paraben) | 0.4 |
| Iodopropynylbutylcarbamate | 0.05 |
| 2-Ethylhexylglycerin | 0.5 |
| Polyacrylic acid (Carbomer) | 0.2 |
| Nylon microparticles | 1 |
| Glycerin | 10 |
| Additives (distarch phosphate, EDTA, BHT) | 0.5 |
| Perfume | q.s. |
| Water | ad 100 |

Example 8
O/W cream

| | % by weight |
|---|---|
| Polyglyceryl-3-methylglucose distearate | 3 |
| Cetyl alcohol | 3 |
| $C_{12-15}$ Alkyl benzoate | 2 |
| Butylene glycol dicaprylate/dicaprate | 2 |
| Caprylic acid/capric acid triglycerides | 2 |
| Hydrogenated polydecene | 1 |
| Dimethylpolysiloxane (dimethicone) | 1 |
| Isodecyl neopentanoate | 4 |
| Bis-ethylhexyloxyphenol-methoxyphenyltriazine | 1 |
| Ethylhexyl methoxycinnamate | 5 |
| Licochalcone A | 0.005 |
| Sodium ascorbylphosphate | 0.1 |
| EDTA | 0.2 |
| Phenoxyethanol | 0.4 |
| Iodopropynylbutylcarbamate | 0.05 |
| p-Hydroxybenzoic acid alkyl ester (paraben) | 0.4 |
| Ethanol denaturated | 2 |
| Carbomer | 0.2 |
| Glycerin | 5 |
| Additives (distarch phosphate, talc, BHT) | 0.2 |
| Perfume | q.s. |
| Water | ad 100 |

Example 9
O/W Cream

| | % by weight |
|---|---|
| Cetearyl glucoside | 2 |
| Myristyl myristate | 1 |
| Stearyl alcohol | 4 |
| $C_{12-15}$ Alkyl benzoate | 2 |
| Caprylic acid/capric acid triglycerides | 3 |
| Hydrogenated polydecene | 1 |
| Dicaprylyl carbonate | 3 |
| Polydecene | 4 |
| Ethylhexyl methoxycinnamate | 3 |
| Ethylhexyl cyanodiphenylacrylate (octocrylene) | 3 |
| Butyl methoxydibenzoylmethane | 2 |
| Licochalcone A | 0.01 |
| Ubiquinone (Q10) | 0.1 |
| Tocopheryl acetate | 1 |
| Trisodium EDTA | 0.1 |
| Phenoxyethanol | 0.7 |
| p-Hydroxybenzoic acid alkyl ester (paraben) | 0.4 |
| Ethylhexylglycerin | 0.4 |
| Xanthan gum | 0.1 |
| Carrageenan | 0.1 |
| Aluminum starch octenylsuccinates | 1 |
| Glycerin | 6 |
| Butylene glycol | 2 |
| Additives (talc, BHT, dye) | 1 |
| Perfume | q.s. |
| Water | ad 100 |

Example 10
W/O Cream

| | % by weight |
|---|---|
| Polyglyceryl-3-diisostearate | 5.0 |
| Polyglyceryl-2-dipolyhydroxystearate | 2.5 |
| Cetearyl alcohol | 2 |
| Cetyl alcohol | 2 |
| $C_{12-15}$ Alkyl benzoate | 8 |
| Caprylic acid/capric acid triglycerides | 6 |
| Octyldodecanol | 5 |
| Octamethyltetrasiloxane (cyclomethicone) | 2 |
| Lactic acid | 5 |
| Citric acid sodium salt | 0.5 |
| Butyl methoxydibenzoylmethane | 1 |
| Ethylhexyl triazone | 1 |
| Ethylhexyl methoxycinnamate | 5 |
| Licochalcone A | 0.001 |
| Campesterol | 0.01 |
| Retinyl palmitate | 0.05 |
| Phenoxyethanol | 0.4 |
| p-Hydroxybenzoic acid alkyl ester (paraben) | 0.1 |
| Glycerin | 7 |
| Fillers (EDTA, aluminum stearate, BHT) | 0.6 |
| Perfume | q.s. |
| Water | ad 100 |

Example 11
Microemulsion

| | % by weight |
|---|---|
| Lecithin | 1.8 |
| PEG-50 hydrogenated castor oil isostearate | 5.2 |
| Dicaprylyl ether | 7.0 |
| Phenoxyethanol | 0.5 |
| p-Hydroxybenzoic acid alkyl ester (paraben) | 0.1 |
| Diazolidinylurea | 0.2 |
| 2-Ethylhexylglycerin | 0.5 |
| Tricontayl PVP | 0.3 |
| Licochalcone A | 0.01 |
| β-Sitosterol | 0.001 |
| Glycerin | 7 |
| Butylene glycol | 3 |
| Additives (talc, BHT, EDTA) | 0.5 |
| Perfume | q.s. |
| Water | ad 100 |

Example 12
Pickering Emulsion

| | % by weight |
|---|---|
| Microcrystalline wax | 4.5 |
| Carnauba wax | 1.5 |
| Candelilla wax | 4.0 |
| Lanolin oil | 4.0 |
| Bis-diglyceryl polyacyladipate-2 | 3.5 |
| Dimethicone | 1.0 |
| Isopropyl palmitate | 3.5 |
| Triisostearin | 3.0 |
| Myristyl lactate | 4.0 |
| Jojoba oil | 2.0 |
| Hydrogenated polydecene | 2.5 |
| Octyldodecanol | 2.5 |
| Licochalcone A | 0.01 |
| Phenoxyethanol | 0.3 |
| Ethylhexyl methoxycinnamate | 2 |
| Butyl methoxydibenzoylmethane | 0.5 |
| Micronized titanium dioxide (Eusolex T 2000) | 2.0 |
| Titanium dioxide CI 77891 | 4.0 |
| Iron oxide CI 77491, 77492, 77499 | 3.2 |
| D&C Red 7 | 0.6 |
| Tocopheryl acetate | 1.0 |
| Xylitol | 2.0 |
| EDTA | 0.2 |
| Glycerin | 5.0 |
| Preservatives, BHT, perfume, aroma | q.s. |
| Water | 30.0 |
| Castor oil | ad 100 |

Example 13
W/O Care Stick

| | % by weight |
|---|---|
| Caprylic acid/capric acid triglycerides | 8 |
| Octyldodecanol | 7 |
| Paraffin oil | 2 |
| Pentaerythrityl tetraisostearate | 2 |
| $C_{12-15}$ Alkyl benzoate | 2 |
| Jojoba oil | 2 |
| PEG-45/dodecyl glycol copolymer | 3 |
| Polyglyceryl-3 diisostearate | 2.5 |
| Sucrose distearate | 0.5 |
| Bis-diglyceryl polyacyladipate-2 | 9 |
| Cetyl palmitate | 2.5 |
| $C_{16-36}$ Alkyl stearates | 14 |
| Carnauba wax | 1.5 |
| Beeswax | 0.5 |
| Ethylhexyl cyanodiphenylacrylate (octocrylene) | 2 |
| Licochalcone A | 0.01 |
| Phenoxyethanol | 0.2 |
| Bismuth oxychloride (BiOCl) | 2 |
| PTFE | 2.5 |
| Pearlescent pigments | 3 |
| Rokonsal S1 | 0.4 |
| Glycerin | 5 |
| Perfume, BHT, neutralizing agents | q.s. |
| Water | ad 100 |

Example 14
W/O Concealer Stick

| | % by weight |
|---|---|
| Caprylic acid/capric acid triglycerides | 5 |
| Octyldodecanol | 5 |
| Pentaerythrityl tetraisostearate | 4 |
| Dimethicone | 0.5 |
| PEG-45/dodecyl glycol copolymer | 3.5 |
| Bis-diglyceryl polyacyladipate-2 | 2 |
| $C_{16-36}$ Alkyl stearate | 1 |
| $C_{20-40}$ Alkyl stearate | 8 |
| Carnauba wax | 1.5 |
| PVP/eicosene copolymer | 1 |
| Micronized titanium dioxide | 2 |
| Octyl methoxycinnamate | 2 |
| Licochalcone A | 0.02 |
| Phenoxyethanol | 0.4 |
| β-Sitosterol | 0.01 |
| Nylon-12 | 3 |
| Lauroyl lysine | 0.5 |
| PMMA | 6 |
| Titanium dioxide coated with $Al_2O_3$ | 7 |
| Iron oxides | 4 |
| Ultramarine | 0.5 |
| Germall II | 0.25 |
| Glycerin | 2 |
| Perfume, BHT, neutralizing agents | q.s. |
| Water | ad 100 |

Example 15
W/O Foundation Stick

| | % by weight |
|---|---|
| Caprylic acid/capric acid triglycerides | 5 |
| Octyldodecanol | 5 |
| Dicaprylyl carbonate | 3 |
| Dicaprylyl ether | 2 |
| Dimethicone | 0.5 |
| PEG-45/dodecyl glycol copolymer | 2 |
| Polyglyceryl-3-diisostearate | 1.5 |
| $C_{16-36}$ Alkyl stearate | 2 |
| $C_{20-40}$ Alkyl stearate | 8 |
| Licochalcone A | 0.002 |
| Phenoxyethanol | 0.3 |
| β-Sitosterol | 0.02 |
| Bismuth oxychloride (BiOCl) | 3 |
| Polymethylsilsesquioxane (Tospearl) | 0.5 |
| PMMA | 3 |
| Titanium dioxide coated with $Al_2O_3$ | 6 |
| Iron oxides | 4 |
| Ultramarine | 0.6 |
| Glycerin | 10 |
| Perfume, BHT, neutralizing agents | q.s. |
| Water | ad 100 |

Example 16
W/O Sunscreen Stick

| | % by weight |
|---|---|
| Caprylic acid/capric acid triglycerides | 8 |
| Octyldodecanol | 8 |
| Pentaerythrityl tetraisostearate | 8 |
| Jojoba oil | 1 |
| Polyglyceryl-3 diisostearate | 2 |
| PEG-30 di-polyhydroxystearate | 2.5 |
| $C_{16-36}$ Alkyl stearate | 1 |
| $C_{20-40}$ Alkyl stearate | 9 |
| PVP/eicosene copolymer | 1 |
| Butyl methoxydibenzoylmethane | 1 |
| Micronized titanium dioxide | 4 |
| Ethylhexyl cyanodiphenylacrylate (octocrylene) | 3.6 |
| Octyl methoxycinnamate | 3.6 |
| Licochalcone A | 0.001 |
| Phenoxyethanol | 0.4 |
| β-Sitosterol | 0.02 |

Example 16
W/O Sunscreen Stick

| | % by weight |
|---|---|
| Boron nitride | 3 |
| Polymethylsilsesquioxane (Tospearl) | 1 |
| Silica LDP | 1 |
| Glydant plus | 0.3 |
| Glycerin | 5 |
| Perfume, BHT, neutralizing agents | q.s. |
| Water | ad 100 |

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A method for the treatment of an inflammatory skin condition in a subject in need thereof, wherein the method comprises applying to skin affected by the inflammatory skin condition a preparation which comprises from about 0.0005% to about 50% by weight of an active substance combination comprising
   (a) licochalcone A,
   (b) phenoxyethanol, and
   (c) optionally, glycerin;
   in an amount which is effective for treating the inflammatory skin condition, wherein the inflammatory skin condition is at least one of seborrheic eczema, polymorphic light dermatosis, psoriasis, and vitiligo.

2. The method of claim 1, wherein licochalcone A is present in the preparation in the form of an extract of radix glycyrrhizae inflatae that comprises licochalcone A.

3. The method of claim 1, wherein the preparation comprises a weight ratio (A:B:C) which is a:b:c, where a, b and c independently of one another represent rational numbers of from about 0.001 to about 200, A represents licochalcone A, B represents phenoxyethanol, and C represents glycerin.

4. The method of claim 3, wherein a, b and c independently of one another represent rational numbers of up to about 10.

5. The method of claim 3, wherein a weight ratio (B+C)/(A*100) is from about 0.5 to about 1,000.

6. The method of claim 1, wherein the preparation comprises from about 0.01% to about 20% by weight of the active substance combination.

7. The method of claim 6, wherein the preparation comprises from about 0.005% to about 0.5% by weight of licochalcone A.

8. The method of claim 7, wherein the preparation comprises from about 0.001% to about 5% by weight of phenoxyethanol.

9. The method of claim 7, wherein the preparation comprises from about 0.1% to about 0.5% by weight of phenoxyethanol.

10. The method of claim 1, wherein the preparation comprises from about 0.001% to about 30% by weight of glycerin.

11. The method of claim 8, wherein the preparation comprises from about 1% to about 8% by weight of glycerin.

12. The method of claim 1, wherein the preparation further comprises from about 0.001% to about 20% by weight of one or more polyols.

13. The method of claim 1, wherein the preparation comprises an emulsion.

14. The method of claim 1, wherein the preparation comprises from about 0.005% to about 0.5% by weight of licochalcone A, from about 0.1% to about 0.5% by weight of phenoxyethanol, and from about 1% to about 8% by weight of glycerin.

* * * * *